US012765775B2

(12) United States Patent
Ach et al.

(10) Patent No.: US 12,765,775 B2
(45) Date of Patent: Oct. 20, 2026

(54) METHOD FOR DETERMINING THE AUTOFLUORESCENCE OF AN OCULAR FUNDUS OF AN EYE BY MEANS OF OPTICAL COHERENCE TOMOGRAPHY

(71) Applicant: Rheinische Friedrich-Wilhelms-Universität Bonn, Bonn (DE)

(72) Inventors: Thomas Ach, Bonn (DE); Leon von der Emde, Alfter (DE)

(73) Assignee: Rheinische Friedrich-Wilhelms-Universität Bonn, Bonn (DE)

( * ) Notice: Subject to any disclaimer, the term of this patent is extended or adjusted under 35 U.S.C. 154(b) by 313 days.

(21) Appl. No.: 18/532,270

(22) Filed: Dec. 7, 2023

(65) Prior Publication Data

US 2024/0188826 A1 Jun. 13, 2024

(30) Foreign Application Priority Data

Dec. 8, 2022 (DE) ..................... 10 2022 132 717.5

(51) Int. Cl.
*A61B 5/00* (2006.01)
*A61B 3/10* (2006.01)
*A61B 3/12* (2006.01)

(52) U.S. Cl.
CPC ............ *A61B 5/0071* (2013.01); *A61B 3/102* (2013.01); *A61B 3/12* (2013.01)

(58) Field of Classification Search
CPC ......... A61B 5/0071; A61B 3/102; A61B 3/12; A61B 3/10
See application file for complete search history.

(56) References Cited

U.S. PATENT DOCUMENTS 4,715,703 A * 12/1987 Cornsweet ............... A61B 3/12 606/4
5,784,162 A * 7/1998 Cabib ..................... G01J 3/453 435/6.12

(Continued)

OTHER PUBLICATIONS

Oishi et al., "Structural Changes in Optical Coherence Tomography Underlying Spots of Increased Autofluorescence in the Perilesional Zone of Geographic Atrophy", Investigative Ophthalmology & Visual Science, vol. 58, No. 7, Jun. 2017, pp. 3303-3310.

*Primary Examiner* — Mustak Choudhury
(74) *Attorney, Agent, or Firm* — Dority & Manning, P.A.

(57) ABSTRACT

A method for determining the autofluorescence of an ocular fundus of an eye includes detecting of an ocular fundus by means of optical coherence tomography and providing of a detected three-dimensional image of the ocular fundus including several retinal layers to an evaluation unit. Furthermore, the method includes dividing the three-dimensional image into a plurality of two-dimensional cross-sections per retinal layer and combining a plurality of cross-sections to form at least one reflectivity map and at least one layer thickness map per retinal layer, with the reflectivity map including the reflectivity of the retinal layer and the layer thickness map comprises the layer thickness of the retinal layer. Additionally, the method includes dividing the reflectivity maps and the layer thickness map each into several pixels, determining at least one reflectivity value and the layer thickness per pixel, and determining an autofluorescence value using the reflectivity value and the layer thickness per pixel.

6 Claims, 2 Drawing Sheets

(56) References Cited

U.S. PATENT DOCUMENTS

Figure 1:
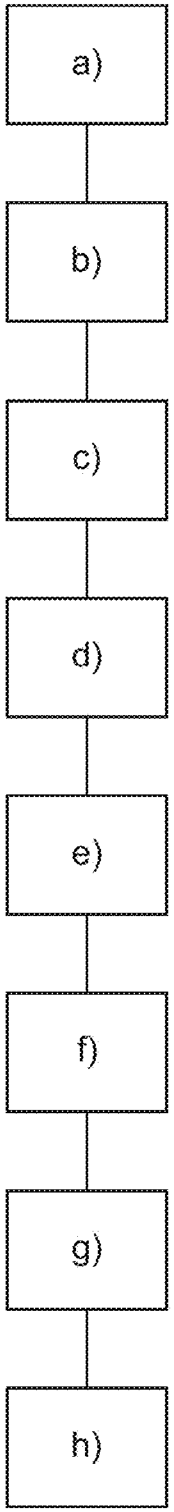

| | | | | |
|---|---|---|---|---|
| 7,257,437 | B2 * | 8/2007 | Demos | A61B 5/0075 600/473 |
| 7,500,751 | B2 * | 3/2009 | Tajima | A61B 3/14 351/221 |
| 8,807,751 | B2 * | 8/2014 | Kahn | A61B 3/10 351/200 |
| 11,432,719 | B2 * | 9/2022 | Huang | G06T 7/168 |
| 2004/0036838 | A1 * | 2/2004 | Podoleanu | A61B 3/102 351/206 |
| 2022/0230300 | A1 * | 7/2022 | Kawczynski | A61B 3/102 |

* cited by examiner

METHOD FOR DETERMINING THE AUTOFLUORESCENCE OF AN OCULAR FUNDUS OF AN EYE BY MEANS OF OPTICAL COHERENCE TOMOGRAPHY

CROSS-REFERENCE TO RELATED APPLICATIONS

The present application is based upon and claims the right of priority to DE Patent Application Number 10 2022 132 717.5, filed Dec. 8, 2022, the disclosure of which is hereby incorporated by reference herein in its entirety for all purposes.

The invention relates to a method for determining the autofluorescence of an ocular fundus of an eye using optical coherence tomography.

Autofluorescence (AF) of the ocular fundus of the eye (fundus autofluorescence, FAF) is a natural phenomenon in which light emitted by the fundus of the eye can be captured and further analyzed after excitation with light of different wavelengths. FAF is important in ophthalmology for the diagnosis and therapy monitoring of retinal diseases.

In clinical examinations, FAF is mainly performed using short-wave light (blue) or long-wave light (near infrared). Fluorescein angiography is also known, for which a suitable dye is injected into the bloodstream as a colorant. Blue FAF images are time-consuming, use very bright, dazzling blue light and require a high number of averages due to the weakness of the autofluorescence signal. The methods known in the state of the art for measuring FAF are complex and associated with long measurement times, making these measurement methods not only time-consuming but also uncomfortable for the patient.

Based on this, it is an object of the invention to provide a method for determining the autofluorescence of the ocular fundus of the eye which is particularly quick and easy to perform and is ubiquitously available.

The object of the invention is achieved by the features of the independent claims. Advantageous embodiments are given in the subclaims.

According to the invention, a method for determining the autofluorescence of an ocular fundus of an eye is thus provided. The method comprises the following method steps:

a) Detecting of an ocular fundus by means of optical coherence tomography and provision of a detected three-dimensional image of the ocular fundus comprising several retinal layers to an evaluation unit, b) Dividing the three-dimensional image into a large number of two-dimensional cross-sections per retinal layer, c) Combining a plurality of cross-sections into at least one reflectivity map and at least one layer thickness map per retinal layer, wherein the reflectivity map comprises the reflectivity of the retinal layer and the layer thickness map comprises the layer thickness of the retinal layer, d) Dividing the reflectivity maps and the layer thickness map each into several pixels, e) Determining at least one reflectivity value and the layer thickness per pixel, f) Determining an autofluorescence value based on the reflectivity value and the layer thickness per pixel.

"Autofluorescence" refers in particular to pseudo-autofluorescence. Pseudo-autofluorescence is determined by indirect detection via the reflectivity, so that the autofluorescence is not detected directly, but is derived as pseudo-autofluorescence.

The term "ocular fundus" refers to the area behind the transparent vitreous body on the inner wall of the eyeball. The ocular fundus includes in particular the retina, the retinal pigment epithelium (RPE) and the bruch membrane.

The AF signal is mainly caused by bisretinoids in granules of the retinal pigment epithelium (RPE). In addition to their autofluorescent properties, the granules also have light-reflecting properties. This plays an important role in structural images of the retina using spectral domain optical coherence tomography (SD-OCT).

SD-OCT is a fast, safe and easy-to-perform examination technique that visualizes the individual retinal layers in almost histological resolution. The RPE in particular has very strong reflective properties due to the more than 1500 granules in the cell body. Different layers reflect the incoming light differently, so that a cross-section of the examined tissue can be calculated and displayed using the information obtained. This type of reconstruction is called tomography.

Procedures such as retinoscopy and fluorescein angiography allow a "top view" of the retina and its structures. However, they do not show the three-dimensional structure of the examined tissue.

The measurement procedure of coherence tomography does not strain the eye, nor is the measurement affected by the vitreous body of the eye.

The autofluorescence is determined on the basis of this reflection image of an SD-OCT scan. It has been shown that a high reflectance behavior corresponds to a high number of intracellular granules and that changes in the reflectance behavior in the RPE lead to changes in autofluorescence.

It is therefore a main aspect of the invention that the reflectivities in the retinal layers are determined by means of coherence tomography, which can be carried out quickly and easily, and autofluorescence is determined as a function of this.

Several two-dimensional cross-sections per retinal layer with a color-coded layer thickness are generated from a three-dimensional volume macula scan. The retinal layers preferably have a predetermined layer thickness. Alternatively, the retinal layer thickness is preferably determined depending on the individual circumstances of a patient. The retinal layer thickness is then determined using white and black lines from histological scans that have a histological correlate. Two-dimensional reflectivity maps and layer thickness maps are created from the cross-sections. In particular, all cross-sections are combined into several reflectivity maps. The layer thickness of the retinal layer is graphically represented in a two-dimensional layer thickness map using a gray scale. The reflectivity map is created by averaging the layer thickness. The reflectivity values, which indicate the reflectivity of the retinal layer, are also displayed graphically using a gray scale. In particular, the thicker the layer for gray-scale layer thickness maps and the higher the reflectivity for gray-scale reflectivity maps, the whiter the representation. This results in so-called en-face maps, preferably four en-face maps per retina layer. The reflectivity maps are divided into a large number of pixels. At least one reflectivity value and one layer thickness are determined for each pixel.

The autofluorescence is determined per pixel using the reflectivity value and the layer thickness.

In the present case, "en-face map" refers to a frontal view of an originally three-dimensional image, whereby one dimension is removed by the frontal view, namely the depth, by bundling or averaging the depth information. In other words, the three-dimensional image is decimated by one dimension by averaging the reflectivity in height or depth and displaying the length graphically.

When the term “reflectivity” is used here, it refers to the ability of the back of the eye or the tissue to reflect incident light. The higher the reflectivity value describing the reflectivity, the higher the proportion of light that is reflected.

The term “autofluorescence” refers to the property of the ocular fundus or tissue to emit light after stimulation. The higher the autofluorescence value describing the autofluorescence, the more light is emitted.

According to a preferred further embodiment of the invention, the method comprises the following further method steps:

g) Providing the autofluorescence values to a visualization unit, h) Visualize the autofluorescence values in at least one autofluorescence map using a gray scale.

The autofluorescence is determined per pixel for the majority of reflectivity maps using the reflectivity value and the layer thickness. The autofluorescence values thus obtained are initially provided numerically. With the help of a visualization unit, the numerical autofluorescence values are displayed graphically on a grey scale so that this graphical representation of the autofluorescence can be evaluated by a physician.

According to a preferred further embodiment of the invention, the reflectivity value comprises a reflectivity maximum per pixel and/or a reflectivity minimum per pixel and/or a reflectivity value per pixel averaged over the layer thickness. Accordingly, up to four key figures are available per pixel for each retinal layer to determine the autofluorescence: The layer thickness, the reflectivity average, the reflectivity maximum and the reflectivity minimum.

According to a preferred further embodiment of the invention, determining the autofluorescence comprises predicting the autofluorescence values on the basis of previously determined target values using weighted decision trees. The term “target values” refers in particular to conventional FAF values. These indicate the autofluorescence in a healthy ocular fundus and were statistically recorded in preparation for the method according to the invention.

The term “decision trees” refers in particular to ordered, directed trees that serve to represent decision rules. The graphical representation as a tree diagram illustrates hierarchically sequential decisions. They are important in numerous areas in which automatic classification is used or formal rules are derived or represented from empirical knowledge. Decision trees are a method for automatically classifying data objects and thus for solving decision problems. A decision tree always consists of a root node and any number of inner nodes as well as at least two leaves. Each node represents a logical rule and each leaf represents an answer to the decision problem.

In this case, the decision problem is the presence or level of autofluorescence. Using different weightings of the nodes, the autofluorescence values can be determined based on the reflectivity values and the layer thickness per pixel.

According to an alternative further embodiment of the invention the determination of the autofluorescence values comprises the prediction of the autofluorescence values by means of an artificial neural network. The artificial neural network is trained to generate the required key figures from the three-dimensional scan by means of optical coherence tomography and to estimate the autofluorescence on this basis.

The number of cross-sections per reflectivity map can preferably be freely selected. According to a preferred further embodiment of the invention each reflectivity map comprises 40 summarized cross-sections of a retinal layer averaged over 10 layers. The number of cross-sections generated from the volume macula scan is preferably more than 100 cross-sections. An autofluorescence value is determined pixel by pixel for each reflectivity map, so that the autofluorescence values are summarized and displayed via at least one autofluorescence map or predicted pseudo-FAF map (inferred BAF).

According to the invention, the use of reflectivities of an ocular fundus obtained by means of optical coherence tomography for determining an autofluorescence of the ocular fundus is also provided. Surprisingly, it has been shown that the reflectivities of the ocular fundus can be used to make a statement about the autofluorescence. A change in reflectance behavior leads to changes in autofluorescence.

In the following, the invention is described in further detail with reference to the drawings showing preferred exemplary embodiments.

The drawings show

Figure 2:
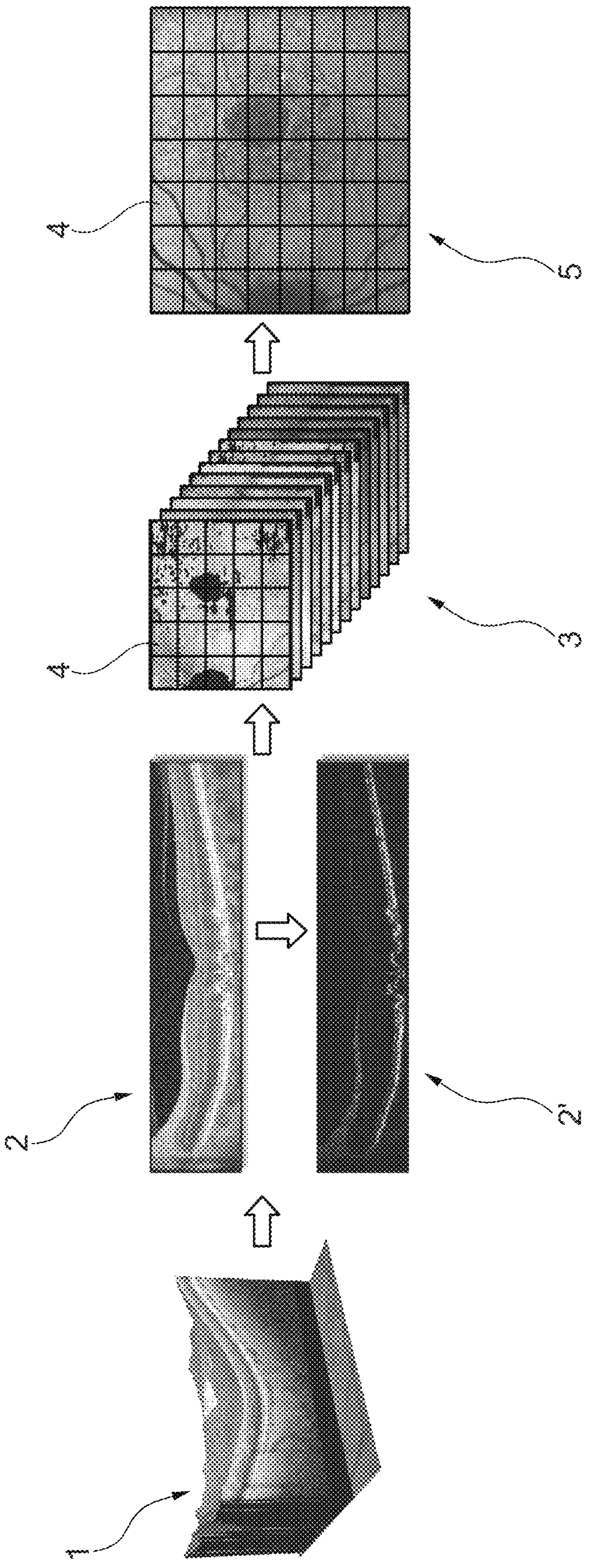

FIG. 1 schematically a method for determining autofluorescence according to a preferred embodiment of the invention, FIG. 2 schematically a representation of the various stages of the method according to a preferred embodiment of the invention.

FIG. 1 schematically shows a method for determining autofluorescence according to a preferred embodiment of the invention. First, the ocular fundus of an eye is captured using optical coherence tomography so that the captured three-dimensional image 1 of the volume macula scan can be provided to an evaluation unit a).

The three-dimensional image 1 is then divided into a large number of two-dimensional cross-sections 2 with the different retinal layers (B-scan) b). From the cross-sections, 10 maps are created for each retinal layer, which represent the retinal layer thickness and reflectivity on a gray scale c). This results in several reflectivity maps 3 and one layer thickness map per retinal layer.

These reflectivity maps 3 are each divided into several pixels 4 d). A reflectivity value is then determined for each reflectivity map 3 and each pixel 4 e). This can be the reflectivity averaged over the layer thicknesses and/or a reflectivity maximum or minimum. Based on the reflectivity values determined and the average layer thickness, an autofluorescence value is determined for each pixel f).

The numerical autofluorescence values are then provided to a visualization unit g) so that they can be displayed visually on a grey scale h) and evaluated by a physician.

FIG. 2 shows the individual stages of the procedure described above. First, a three-dimensional image 1 of the fundus of the eye, the so-called volume macula scan, is available.

The three-dimensional image 1 is then divided into a large number of two-dimensional cross-sections 2. These cross-sections or the so-called OCT B-scans are converted from the preset logarithmic representation into the reflectivity patterns in raw format 2'. The reflectivity maps 3 can be created using this raw data.

The reflectivity maps 3 each comprise several cross-sections 2'. The raw data is averaged along the layer thickness. This means that a two-dimensional reflectivity map 3 is generated from the multiple cross-sections with a specific image depth. The reflectivity maps 3 are each divided into several pixels 4. In FIG. 2, the pixel sizes are not drawn to scale. The pixels have a significantly smaller size than shown in FIG. 2.

An autofluorescence value is determined for each pixel based on the reflectivity values and the average layer thickness. The numerical autofluorescence values are summarized in an autofluorescence map 5, which graphically displays the predicted autofluorescence values. This image can be used to determine a pathological change in the fundus of the eye.

LIST OF REFERENCE SYMBOLS

1 Three-dimensional image of the ocular fundus of the eye
2 Cross-sections in logarithmic representation
2' Cross sections in raw format
3 Reflectivity map
4 Pixel
5 Autofluorescence map

The invention claimed is:

1. A method for determining an autofluorescence of an ocular fundus of an eye, comprising the following method steps:

a) detecting of the ocular fundus by means of optical coherence tomography and providing of a detected three-dimensional image of the ocular fundus comprising several retinal layers to an evaluation unit,
b) dividing the three-dimensional image into a plurality of two-dimensional cross-sections per retinal layer,
c) combining a plurality of cross-sections to form at least one reflectivity map and at least one layer thickness map per retinal layer, wherein the reflectivity map comprises a reflectivity of the retinal layer and the layer thickness map comprises a layer thickness of the retinal layer,
d) dividing the reflectivity maps and the layer thickness map each into several pixels,
e) determining at least one reflectivity value and the layer thickness per pixel, and
f) determining the autofluorescence value using the reflectivity value and the layer thickness per pixel.

2. The method according to claim 1 with the following further method steps:

g) providing the autofluorescence values to a visualization unit, and
h) visualizing the autofluorescence values in at least one autofluorescence map using a grey scale.

3. The method according to claim 1, wherein the reflectivity value comprises a reflectivity maximum per pixel and/or a reflectivity minimum per pixel and/or a reflectivity value per pixel averaged over the layer thickness.

4. The method according to claim 1, wherein determining the autofluorescence values comprises predicting the autofluorescence values on a basis of predetermined target values by means of weighted decision trees.

5. The method according to claim 1, wherein determining the autofluorescence values comprises predicting the autofluorescence values by means of an artificial neural network.

6. The method according to claim 1, wherein 40 cross-sections are combined to form a reflectivity map.

* * * * *